US012565672B2

(12) United States Patent
Ichiyanagi

(10) Patent No.: US 12,565,672 B2
(45) Date of Patent: Mar. 3, 2026

(54) SAMPLING METHOD AND KIT FOR HISTAMINE MEASUREMENT

(71) Applicant: Kikkoman Corporation, Chiba (JP)

(72) Inventor: Yuko Ichiyanagi, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 1184 days.

(21) Appl. No.: 17/269,100

(22) PCT Filed: Aug. 20, 2019

(86) PCT No.: PCT/JP2019/032376

§ 371 (c)(1),
(2) Date: Feb. 17, 2021

(87) PCT Pub. No.: WO2020/040116

PCT Pub. Date: Feb. 27, 2020

(65) Prior Publication Data

US 2021/0310042 A1 Oct. 7, 2021

(30) Foreign Application Priority Data

Aug. 20, 2018 (JP) ................................ 2018-153819

(51) Int. Cl.

| | |
|---|---|
| ***C12Q 1/32*** | (2006.01) |
| ***G01N 33/12*** | (2006.01) |
| ***G01N 33/52*** | (2006.01) |
| ***G01N 33/543*** | (2006.01) |
| ***G01N 33/68*** | (2006.01) |
| ***G01N 33/94*** | (2006.01) |

(52) U.S. Cl.

CPC ............... *C12Q 1/32* (2013.01); *G01N 33/12* (2013.01); *G01N 33/52* (2013.01); *G01N 33/543* (2013.01); *G01N 33/54387* (2021.08); *G01N 33/68* (2013.01); *G01N 33/9406* (2013.01); *G01N 2333/90638* (2013.01)

(58) Field of Classification Search

CPC .......... C12Q 1/32; C12Q 1/005; G01N 33/12; G01N 33/52; G01N 33/543; G01N 33/54387; G01N 33/68; G01N 2333/90638; G01N 2800/42; G01N 33/558; G01N 33/9406; G01N 2333/4603

See application file for complete search history.

(56) References Cited

U.S. PATENT DOCUMENTS

| | | | | |
|---|---|---|---|---|
| 8,420,054 | B2 * | 4/2013 | Schwartz | G01N 33/6881 424/9.1 |
| 2007/0243625 | A1 | 10/2007 | Oguri | |
| 2008/0153079 | A1 * | 6/2008 | Leech | G01N 33/02 435/287.4 |
| 2014/0099656 | A1 * | 4/2014 | Krebs | C12Q 1/32 435/26 |
| 2015/0072338 | A1 | 3/2015 | Holmes | |
| 2015/0072362 | A1 | 3/2015 | Lui et al. | |
| 2017/0219549 | A1 | 8/2017 | Lam | |

FOREIGN PATENT DOCUMENTS

| | | | | |
|---|---|---|---|---|
| EP | 1 767 938 | | | 3/2007 |
| JP | 2001-99803 | | | 4/2001 |
| JP | 2001-157597 | | | 6/2001 |
| JP | 2001157597 | A | * | 6/2001 |
| JP | 2003-61650 | | | 3/2003 |
| JP | 2004-129597 | | | 4/2004 |
| JP | 2005-110507 | | | 4/2005 |
| JP | 2005-331381 | | | 12/2005 |
| JP | 2009039015 | A | * | 2/2009 |
| JP | 2009-236893 | | | 10/2009 |
| JP | 2012-159440 | | | 8/2012 |
| JP | 2016-537009 | | | 12/2016 |
| WO | 2014/171891 | | | 10/2014 |

OTHER PUBLICATIONS

Machine Translation of JP-2009039015-A, originally published Feb. 26, 2009, generated using Patent Translation from Espacenet. Accessed on Jul. 9, 2024 (Year: 2009).*

Sato et al. 2005. "Simple and rapid determination of histamine in food using a new histamine dehydrogenase from *Rhizobium* sp." Analytical biochemistry, 346(2), 320-326., filed Oct. 10, 2023 (Year: 2005).*

Hungerford et al. 2012. "Comparison study of three rapid test kits for histamine in fish: BiooScientific MaxSignal enzymatic assay, Neogen Veratox ELISA, and the Neogen Reveal Histamine Screening test." Food Control, 25(2), 448-457. (Year: 2012).*

Gagic et al. 2019. "Current Trends in Detection of Histamine in Food and Beverages", Journal of Agricultural and Food Chemistry, 67(3), 773-783. DOI: 10.1021/acs.jafc.8b05515 (Year: 2019).*

International Search Report (ISR) issued Nov. 19, 2019 in International (PCT) Application No. PCT/JP2019/032376.

Communication pursuant to Article 94(3) EPC issued Nov. 24, 2022 in corresponding European Patent Application No. 19851670.0.

Communication pursuant to Article 94(3) EPC issued Jul. 17, 2023 in corresponding European Patent Application No. 19 851 670.0.

Sato, T., et al., "Simple and rapid determination of histamine in food using a new histamine dehydrogenase from *Rhizobium* sp.", Analytical Biochemistry, 2005, vol. 346, pp. 320-326.

Luo, L., et al., "A sensitivity-enhanced heterologous immunochromatographic assay based on a monoclonal antibody for the rapid detection of histamine in saury samples", RSC Advances, 2015, vol. 5, pp. 78833-78840.

Extended European Search Report issued Mar. 23, 2022 in corresponding European Patent Application No. EP 19851670.

Xiaotong Feng et al., "A facile molecularly imprinted polymer-based fluorometric assay for detection of histamine", RSC Advances, vol. 8, No. 5, pp. 2365-2372, Jan. 2018.

* cited by examiner

*Primary Examiner* — Anand U Desai
*Assistant Examiner* — Andrew T Moehlman
(74) *Attorney, Agent, or Firm* — Wenderoth, Lind & Ponack, L.L.P.

(57) ABSTRACT

An object of the present invention is to provide a convenient sampling method and kit for histamine measurement. The present invention provides a method and a kit which involve non-invasively sampling a specimen, and detecting histamine from the obtained sample.

4 Claims, 4 Drawing Sheets

SAMPLING METHOD AND KIT FOR HISTAMINE MEASUREMENT

TECHNICAL FIELD

The present invention relates to a sampling method and kit for histamine measurement, etc.

BACKGROUND ART

Histamine is a chemical mediator of allergic reactions that occur in the body. Therefore, allergy-like poisoning is caused by the ingestion of foods containing histamine accumulated in large amounts. As specific symptoms of allergic reactions caused by histamine, the face and the like become red several minutes to several hours after meals, followed by itchiness, hives, or eczema. In severe cases, hives spread throughout the body and may cause bronchitis or a decrease in blood pressure. Thus, histamine measurement methods that can measure histamine content readily and rapidly have been strongly demanded for food processing plants, food sanitation monitoring agencies, clinical laboratories, etc.

For example, in lean fish or processing steps thereof, histamine-producing microbes are capable of acting to produce and accumulate histamine. The eating of foods rich in histamine causes allergy-like poisoning, which is also referred to as histamine food poisoning. It is important to confirm before processing that histamine contents in cooking ingredients are equal to or smaller than a given level. However, whether fish meat contains large amounts of histamine does not necessarily correlate with the putridity of the fish meat and therefore, may not be determined from only smell such as so-called putrid smell. Therefore, histamine measurement is required, aside from freshness measurement of fish meat.

As methods for measuring histamine contents, methods such as fluorescent analysis, chromatography based on thin-layer chromatography or paper chromatography, high-performance liquid chromatography (HPLC), antigen-antibody reaction, and enzymatic techniques are known. The present applicant has focused on enzymatic techniques, which are convenient and highly accurate, and has developed methods for measuring histamine using histamine dehydrogenase in the past (Patent Literatures 1 and 2).

For examination of determining the cause of histamine food poisoning, HPLC or fluorophotometry is typically used. However, these methods require time for examination and are unsuitable for rapid examination for preventing histamine food poisoning. Furthermore, the examination is labor intensive such as by requiring a necessary step of derivatizing histamine by fluorescent labeling, and full inspection of all specimens is difficult.

CITATION LIST

Patent Literature

Patent Literature 1: JP Patent Publication (Kokai) No. 2001-157597 A (2001) (JP Patent No. 3926071)

Patent Literature 2: JP Patent Publication (Kokai) No. 2004-129597 A (2004)

SUMMARY OF INVENTION

Technical Problem

The histamine measurement methods using histamine dehydrogenase, developed and employed by the present applicant (Patent Literatures 1 and 2) require mincing an edible part such as fish meat, and then measuring histamine. If such edible part is minced, use of the specimen (individual fish) is limited because the specimen (analyte) cannot be sold or would be difficult to be sold as a commercial product. Furthermore, the histamine measurement requires labor in that part of the edible parts must be minced. Since conventional histamine examination is invasive due to the mincing of edible parts, etc., not only was full inspection of all specimens (100% tests) substantially impossible, but also the number of specimens (subjects) that can be examined was limited, and frequency of examination was low.

Thus, an object of the present invention is to provide a histamine measurement method and kit capable of solving at least some of the problems described above.

Solution to Problem

In light of the problems described above, the present inventor has completed the present invention by finding that the presence or absence of histamine in an edible part contained in a specimen (analyte) can be determined without destroying the specimen (subject), by non-invasively sampling the specimen for measuring a histamine content, and subjecting the test sample thus obtained to a histamine measurement test.

The present invention encompasses the following aspects.

[1] A histamine measurement method for the examination of histamine food poisoning or for the prevention of histamine food poisoning, comprising the steps of:

(i) non-invasively sampling a specimen to obtain a sample for measurement from the specimen; and (ii) subjecting the sample obtained by the sampling in step (i) to histamine measurement.

[2] The method according to embodiment 1, wherein when the specimen is a fish, the non-invasive sampling is performed from the mouth, from a gill slit, from the anus, on the surface of the fish body, or on the surface of a cut of fish meat that is not minced, of the fish, or when the specimen is a chicken, the non-invasive sampling is performed from the mouth, from the anus, or on the surface of a cut of chicken meat that is not minced, of the chicken.

[3] The method according to embodiment 1 or 2, wherein the non-invasive sampling is performed by swabbing using a cotton tipped swab.

[4] The method according to any one of embodiments 1 to 3, wherein the histamine measurement is histamine measurement by colorimetry using histamine dehydrogenase or immunochromatography using an anti-histamine antibody.

[5] The method according to any one of embodiments 1 to 3, wherein the histamine measurement is colorimetry using histamine dehydrogenase and an error reaction suppressor is further used.

[6] A histamine measurement kit for performing a histamine measurement method according to any one of embodiments 1 to 5, comprising an instruction for use and a reagent for histamine measurement, wherein the instruction for use states that sampling from a specimen is to be performed non-invasively.

[7] A histamine measurement kit for the examination of histamine food poisoning, comprising a sample collection part, a reaction part, and an instruction for use, wherein the reaction part comprises a histamine measurement reagent, and the instruction for use states that sampling from a specimen is to be performed non-invasively.

[8] The kit according to embodiment 7, wherein the histamine measurement reagent comprises histamine dehydrogenase and a reagent for colorimetry, or an anti-histamine antibody and a reagent for immunochromatography.

[9] The kit according to embodiment 7, wherein the histamine measurement reagent comprises histamine dehydrogenase, a reagent for colorimetry and an error reaction suppressor.

[10] A histamine measurement apparatus for the examination of histamine food poisoning, wherein the histamine measurement apparatus comprises a sample collection part, a reaction part, and a sensor part and is accompanied by an instruction for use and wherein the reaction part comprises histamine dehydrogenase, wherein the instruction for use states that sampling from a specimen is to be performed non-invasively, and wherein the sensor part comprises a sensor for the electrochemical measurement of histamine.

[11] Any of the above embodiments, wherein the error reaction suppressor is selected from the group consisting of:

(A)

(i-a) boric acid or a salt thereof, and/or a boronic acid represented by the following formula (I) or (II):

[Formula 1]

(I)

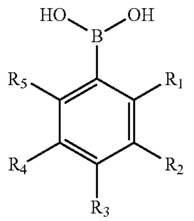

or (II)

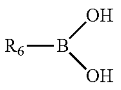

wherein $R_1$ to $R_5$ are each independently selected from the group consisting of H, a boronyl group, a halogen group, a hydroxy group, a carboxy group, a nitro group, an amino group, a sulfo group, a thiol group, a tert-butoxycarbonylamino group, and a substituted or unsubstituted $C_1$ to $C_{10}$ alkyl group, alkenyl group, or alkynyl group, and $R_6$ is selected from the group consisting of a $C_1$ to $C_{10}$ alkyl group, alkenyl group, and alkynyl group substituted with at least one substituent selected from the group consisting of a boronyl group, a halogen group, a hydroxy group, a carboxy group, a nitro group, an amino group, a sulfo group and a thiol group, or an unsubstituted $C_1$ to $C_{10}$ alkyl group, alkenyl group, and alkynyl group or a salt thereof, and/or (i-b) alkyl sulfate;

(B) a buffer containing a compound having a zwitterion and having no carboxy group, the buffer being selected from the group consisting of BES, MOPS, TES, HEPES, EPPS, TAPS, CHES, CAPS, TAPSO, POPSO, HEPPSO, ACES, Bis-Tris, MES, MOPSO, and PIPES, or Tris (tris(hydroxymethyl)aminomethane) or a carbonate buffer;

(C) a buffer containing a compound having a zwitterion and having a sulfo group, the buffer being selected from the group consisting of BES, MOPS, TES, HEPES, EPPS, TAPS, CHES, CAPS, TAPSO, POPSO, HEPPSO, ACES, MES, MOPSO, and PIPES; and (D) a buffer containing a compound having a zwitterion, having a sulfo group, and having a hydroxy group at position 2, the buffer being selected from the group consisting of TAPSO, POPSO, HEPPSO, and MOPSO.

The present specification encompasses the contents disclosed in Japanese Patent Application No. 2018-153819 on which the priority of the present application is based.

Advantageous Effects of Invention

According to the present invention, histamine contained in a specimen can be measured without destroying the specimen.

BRIEF DESCRIPTION OF DRAWINGS

FIG. 1A shows visual color changes. FIG. 1B shows a calibration curve of K values and histamine contents when color was digitized.

DESCRIPTION OF EMBODIMENTS

1. Sampling Method for Histamine Measurement

Figure 1A:
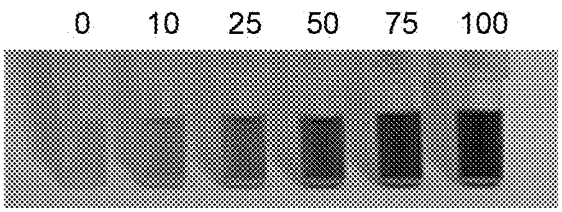
FIGS. 1A and 1B show results of measuring histamine contents at 0 to 100 ppm.

In an embodiment, the present invention provides a sampling method for histamine measurement. In the present specification, histamine also includes a salt thereof. In an embodiment, sampling is performed on a specimen which may contain histamine. Specimens (analytes) which may contain histamine include fish, liquid and solid foods such as fish meat that is not minced (e.g., cuts of fish that are not minced, and cuts of filleted fish), livestock meat, chicken meat, cheese, soy sauce, fish sauce and wine, body fluids such as urine and plasma, biological materials, and living tissues.

In an embodiment, the present invention provides a non-invasive sampling method for histamine measurement. In another embodiment, the present invention provides a histamine measurement method comprising the steps of:

(i) non-invasively sampling a specimen to obtain a sample for measurement from the specimen; and (ii) subjecting the sample obtained by the sampling in step (i) to histamine measurement.

This method can be used, for example, for examining histamine food poisoning or for preventing histamine food poisoning.

In an embodiment, the sampling is performed non-invasively for measuring the histamine content of the specimen. In the present specification, the term "non-invasively performing sampling", "non-invasively sampling", or "non-invasive sampling" means that a sample for measurement is collected without damaging the specimen for the sampling, for example, without mincing fish meal. In the present specification, the "non-invasive sampling" can be any approach that does not further damage a target sample for the sampling. The non-invasive sampling described in the present specification also encompasses the sampling of an already damaged sample, for example, a cut fish or a filleted fish, without further damaging the sample. For example, the sampling of a cut fish, a filleted fish, or chicken meat by the swabbing of its surface falls under (amounts to) the "non-invasive sampling" described in the present specification.

In an embodiment, when the specimen (analyte) is a fish, the non-invasive sampling can be performed on the mouth, the pharynx, the oral cavity, the esophagus, the stomach, the anus, the guts, a gill slit, the gills, fish body surface, or the surface of a cut of fish meat that is not minced, of the fish. In an embodiment, when the specimen is chicken meat, non-invasive sampling can be performed on the surface of a cut of chicken meat that is not minced. As for an unprocessed chicken, the non-invasive sampling can be performed on the mouth, the pharynx, the oral cavity, the esophagus, the stomach, the anus, and the guts of the chicken. The mouth, the oral cavity, the pharynx, the esophagus, or the stomach may be non-invasively sampled by inserting a sampling instrument from the mouth. Alternatively, the anus or the guts may be non-invasively sampled by inserting a sampling instrument from the anus. Further, the gills may be non-invasively sampled by inserting a sampling instrument from a gill slit.

The term "non-invasive", as a medical term, is sometimes used for an approach that does not require the insertion of an instrument to an opening of the body or into the skin. However, the present invention relates to a histamine measurement method predominantly for a specimen such as a fish or a chicken on the premise of being eaten, not a medical examination method on human patients. As such, even an approach which involves inserting a sampling instrument into a specimen from the mouth, a gill slit or the anus is defined to fall under the "non-invasive sampling" described in the present specification. In the present specification, non-invasive sampling is also referred to as sampling that does not comprise the step of destroying a specimen or a portion of a specimen, or sampling that does not substantially destroy a specimen. Although the phrase "not substantially destroy a specimen" means that as a primary rule the specimen is not (to be) destroyed, as an exception slight destruction is acceptable so long as the edibility of the specimen to be eaten is not impaired, an edible part of the specimen to be eaten is not impaired, or the commodity value, such as appearance, of the specimen to be eaten is not impaired. Such minor destruction of the specimen is also encompassed by the phrase "not substantially destroy a specimen" as referred to in the present specification. For example, when the gills of a fish are not a generally eaten site, it is believed that the fish presents few problems as a food or as a commercial product even if slight damage occurs on the gills due to sampling from a gill slit. Thus, such sampling is also encompassed by the non-invasive sampling described in the present specification. The same applies to sampling from the mouth or the anus.

In an embodiment, the non-invasive sampling can be performed by swabbing.

In an embodiment, the histamine measurement can be performed by colorimetry using histamine dehydrogenase or immunochromatography using an anti-histamine antibody. In an embodiment, the histamine measurement method of the present invention does not comprise the step of mincing a sample for the purpose of measuring histamine.

In an embodiment, the present invention provides a histamine measurement kit for performing the histamine measurement method according to the present invention, comprising an instruction for use and a reagent for histamine measurement. In one embodiment, the instruction for use states that sampling from a specimen is to be performed non-invasively. In one embodiment, the reagent for histamine measurement comprises histamine dehydrogenase and a reagent for colorimetry. In another embodiment, the reagent for histamine measurement comprises an anti-histamine antibody and a reagent for immunochromatography. In an embodiment, the reagent for histamine measurement included in this kit may comprise an error reaction suppressor (error reaction inhibitor).

In an embodiment, the present invention provides a method for examining histamine food poisoning and a method for preventing histamine food poisoning using the histamine measurement method or kit of the present invention.

In the present specification, the "histamine dehydrogenase" is an enzyme that is classified into oxidoreductase and catalyzes the oxidation of histamine through the following reaction:

[Formula 2]

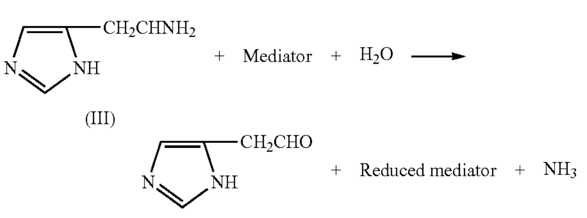

(III)

(IV)

In the reaction formula above, the compound of formula (III) is histamine, and the compound of formula (IV) is 4-imidazolylacetaldehyde. In one embodiment, the mediator is a mediator described in the present specification, for example, PMS (phenazinium methyl sulfate). In this case, the reduced mediator is reduced PMS ($PMSH_2$).

From the perspective of measurement accuracy, the histamine dehydrogenase preferably acts specifically on histamine. In other words, it is preferred that the histamine dehydrogenase specifically acts on histamine without acing on other amines or acts only weakly on other amines. It is particularly preferred that the histamine dehydrogenase acts on histamine without acting on cadaverine or putrescine. The histamine dehydrogenase is preferably derived from a bacterium, for example, a bacterium belonging to the genus *Rhizobium*. The histamine dehydrogenase may be obtained by extracting and/or purifying a naturally derived one or may be produced by a genetic engineering approach known in the art based on genetic information of an organism. Specific methods for producing the histamine dehydrogenase are known to those skilled in the art. For example, a method described in JP Patent Publication (Kokai) No. 2001-157597 A (2001) can be used. Specific examples of the histamine dehydrogenase that can be used in the present invention include histamine dehydrogenase described in JP Patent Publication (Kokai) No. 2001-157597 A (2001). In one embodiment, in the kit of the present invention, the final concentration of the histamine dehydrogenase at the time of measurement or storage, preferably at the time of measurement, is not limited and can be 1 mU/assay to 20 U/assay, preferably 5 ml/assay to 2 U/assay, more preferably 10 mU/assay to 0.5 U/assay, further preferably 25 mU/assay to 0.25 W/assay (wherein 1 U is defined as the amount of the enzyme that produces 1 μmol 4-imidazolylacetaldehyde at 37° C. at pH 9.0 for 1 minute). The concentration of the histamine dehydrogenase described above is given for illustrative purposes and can be appropriately adjusted according to the reaction time.

In an embodiment, the histamine measurement method of the present invention may employ an error reaction suppressor. The error reaction suppressor that can be used in the present invention may be selected from the group consisting of:

(A)

(i-a) boric acid or a salt thereof, and/or a boronic acid represented by the following formula (I) or (II):

[Formula 3]

(I)

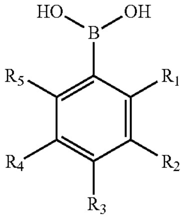

or (II)

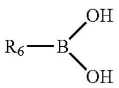

wherein $R_1$ to $R_5$ are each independently selected from the group consisting of H, a boronyl group, a halogen group, a hydroxy group, a carboxy group, a nitro group, an amino group, a sulfo group, a thiol group, a tert-butoxycarbonylamino group, and a substituted or unsubstituted $C_1$ to $C_{10}$ alkyl group, alkenyl group, or alkynyl group, and $R_6$ is selected from the group consisting of a $C_1$ to $C_{10}$ alkyl group, alkenyl group, and alkynyl group substituted with at least one substituent selected from the group consisting of a boronyl group, a halogen group, a hydroxy group, a carboxy group, a nitro group, an amino group, a sulfo group and a thiol group, or an unsubstituted $C_1$ to $C_{10}$ alkyl group, alkenyl group, and alkynyl group or a salt thereof, and/or (i-b) alkyl sulfate;

(B) a buffer containing a compound having a zwitterion and having no carboxy group, wherein the buffer is selected from the group consisting of BES, MOPS, TES, HEPES, EPPS, TAPS, CHES, CAPS, TAPSO, POPSO, HEPPSO, ACES, Bis-Tris, MES, MOPSO, and PIPES, or Tris (tris(hydroxymethyl)aminomethane) or a carbonate buffer;

(C) a buffer containing a compound having a zwitterion and having a sulfo group, wherein the buffer is selected from the group consisting of BES, MOPS, TES, HEPES, EPPS, TAPS, CHES, CAPS, TAPSO, POPSO, HEPPSO, ACES, MES, MOPSO, and PIPES; and (D) a buffer containing a compound having a zwitterion, having a sulfo group, and having a hydroxy group at position 2, wherein the buffer is selected from the group consisting of TAPSO, POPSO, HEPPSO, and MOPSO.

In the present specification, "boric acid" means an oxo acid of boron represented by the chemical formula $B(OH)_3$. In the present specification, a "boronic acid" is obtained by the substitution of a hydroxy group in boric acid and may mean a compound represented by the following formula (I) or (II):

[Formula 1]

(I)

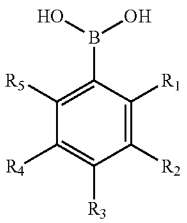

or (II)

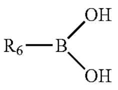

wherein $R_1$ to $R_5$ are each independently selected from the group consisting of H, a boronyl group, a halogen group, a hydroxy group, a carboxy group, a nitro group, an amino group, a sulfo group, a thiol group, a tert-butoxycarbonylamino group, and a substituted or unsubstituted $C_1$ to $C_{10}$ (e.g., $C_1$ to $C_8$, $C_1$ to $C_6$, or $C_1$ to $C_4$) alkyl group, alkenyl group, or alkynyl group, and $R_6$ is selected from the group consisting of a $C_1$ to $C_{10}$ (e.g., $C_1$ to $C_8$, $C_1$ to $C_6$, or $C_1$ to $C_4$) alkyl group, alkenyl group, or alkynyl group substituted with at least one substituent selected from the group consisting of a boronyl group, a halogen group, a hydroxy group, a carboxy group, a nitro group, an amino group, a sulfo group and a thiol group, or an unsubstituted $C_1$ to $C_{10}$ (e.g., $C_1$ to $C_8$, $C_1$ to $C_6$, or $C_1$ to $C_4$) alkyl group, alkenyl group, or alkynyl group.

In the compound of formula (I), at least one of $R_1$ to $R_5$ is a halogen group, preferably fluorine or chlorine, or a tert-butoxycarbonylamino group. In the present specification, examples of the boronic acid include, but are not limited to, butylboronic acid, 4-chlorophenylboronic acid, 4-fluorophenylboronic acid, and 3-[(tert-butoxycarbonyl) amino]phenylboronic acid.

In the present specification, "salt" refers to a salt of an active compound prepared using a base or an acid based on a particular substituent (e.g., a hydroxy group) of a compound. The salt can be classified into a base-addition salt and an acid-addition salt depending on the base or the acid used.

Examples of the "base-addition salt" include: alkali metal salts such as sodium salt and potassium salt: alkaline earth metal salts such as calcium salt and magnesium salt; aliphatic amine salts such as trimethylamine salt, ethanolamine salt, and procaine salt; aralkylamine salts such as N,N-dibenzylethylenediamine; heterocyclic aromatic amine salts such as pyridine salt; basic amino acid salts such as arginine salt; quaternary ammonium salts such as tetramethylammonium salt, tetraethylammonium salt, and benzyl trimethylammonium salt; and ammonium salts.

Examples of the "acid-addition salt" include: inorganic acid salts such as hydrochloride, sulfate, nitrate, phosphate, carbonate, bicarbonate, and perchlorate; organic acid salts such as acetate, propionate, lactate, maleate, fumarate, tartrate, malate, citrate, and ascorbate; sulfonates such as methanesulfonate, isethionate, benzenesulfonate, and p-toluenesulfonate; and acidic amino acid salts such as aspartate and glutamate.

In the present invention, the concentration of boric acid or a salt thereof, and/or the boronic acid or a salt thereof is not particularly limited as long as the concentration is capable of reducing error reaction that is not derived from the oxidation of histamine by histamine dehydrogenase (in the present specification, also simply referred to as "error reaction"). Such concentration can be readily determined by those skilled in the art with reference to the description of the present specification. As an example, the final concentration of boric acid or a salt thereof, and/or the boronic acid or a salt thereof at the time of measurement or storage, preferably at the time of measurement, can be 5 mM or higher, 10 mM or higher, 20 mM or higher, 25 mM or higher, 50 mM or higher, 80 mM or higher, or 100 mM or higher, and is a concentration of, for example, 1000 mM or lower, 500 mM or lower, 400 mM or lower, 300 mM or lower, 200 mM or lower, 150 mM or lower, or 120 mM or lower. The final concentration (thereof) at the time of measurement or storage can be, for example, 5 mM to 1000 mM, 25 mM to 300 mM, or 50 mM to 200 mM.

In the present invention, the type of the alkyl sulfate is not particularly limited as long as the type is capable of reducing error reaction. The alkyl sulfate can be one or more members selected from the group consisting of, for example, alkyl sulfuric acid ester salts such as sodium lauryl sulfate, potassium lauryl sulfate, sodium stearyl sulfate, triethanolamine lauryl sulfate, and ammonium lauryl sulfate; and polyoxyethylene alkyl sulfates such as sodium laureth sulfate and triethanolamine laureth sulfate. The alkyl sulfate is, for example, sodium lauryl sulfate.

In the present invention, the concentration of the alkyl sulfate is not particularly limited as long as the concentration is capable of reducing error reaction. Such a concentration can be readily determined by those skilled in the art with reference to the description of the present specification. As an example, the final concentration of the alkyl sulfate at the time of measurement or storage, preferably at the time of measurement, is 0.01% or higher, 0.05% or higher, preferably 0.1% or higher, 0.5% or higher, or 1% or higher, and 10% or lower, 5% or lower, or 2% or lower. The final concentration (thereof) is a concentration of, for example, approximately 0.05% to 2% or approximately 0.1 to 1%.

In the histamine measurement by colorimetry using histamine dehydrogenase, the degree of error reaction that is not derived from the oxidation of histamine by the histamine dehydrogenase or the degree of reduction or inhibition of the error reaction can be evaluated, for example, by visual inspection or by the comparison of colors digitized using software such as ILLUSTRATOR CS2™ (manufactured by Adobe Inc.), as described in Examples.

In one embodiment, the histamine measurement reagent of the present invention may further comprise a mediator. In the present specification, the "mediator" refers to a molecule that facilitates oxidoreduction reaction catalyzed by histamine dehydrogenase, for example, through action as a cofactor. The mediator is preferably a substance that promotes (facilitates) electron transfer from a substrate to a coloring reagent. An appropriate mediator for a reaction system can be readily selected by those skilled in the art and examples of the mediator include, but are not limited to, I-methoxy PMS (1-methoxy-5-methylphenazinium methyl sulfate), PMS (phenazinium methyl sulfate), PES (phenazinium ethyl sulfate), 1-methoxy PES (1-methoxy-5-ethylphenazinium ethyl sulfate), benzoquinone and derivatives thereof, ferricyanide (potassium or sodium salt), ferrocene and derivatives thereof, dichlorophenolindophenol, naphthoquinone and derivatives thereof, phenanthrolinequinone and derivatives thereof, phenanthrenequinone and derivatives thereof, anthraquinone and derivatives thereof, ruthenium salt, and ruthenium complexes and, further, the mediator is preferably 1-methoxy PMS. PMS, PES or 1-methoxy PES, more preferably I-methoxy PMS. In one embodiment, the measurement reagent of the present invention comprises the mediator having a final concentration of 1 μM or higher, 10 μM or higher, 20 μM or higher, 25 μM or higher, 30 μM or higher, or 35 μM or higher, and 80 μM or lower, 70 μM or lower, 60 μM or lower, 50 μM or lower, or 45 μM or lower, for example, 1 μM to 80 μM, 35 μM to 45 μM or approximately 42 μM, at the time of measurement or storage.

In one embodiment, the histamine measurement reagent of the present invention may further comprise a coloring reagent. The coloring reagent preferably develops a color when histamine is oxidized by histamine dehydrogenase and the presence of histamine can be conveniently detected by observing such color development. Examples of the coloring reagent include tetrazolium salt, for example, WST-4 (2-benzothiazolyl-3-(4-carboxy-2-methoxyphenyl)-5-[4-(2-sulfoethylcarbamoyl)phenyl]-2H-tetrazolium), WST-5 (2,2'-dibenzothiazolyl-5,5'-bis[4-di(2-sulfoethyl)carbamoylphenyl]-3,3'-(3,3'-dimethoxy-4,4'-biphenylene)ditetrazolium, disodium salt), WST-8 (2-(2-methoxy-4-nitrophenyl)-3-(4-nitrophenyl)-5-(2,4-disulfophenyl)-2H-tetrazolium), NBT (3,3'-[3,3'-dimethoxy-(1,1'-biphenyl)-4,4'-diyl]-bis[2-(4-nitrophenyl)-5-phenyl-2H-tetrazolium chloride]), INT (2-(4-iodophenyl)-3-(4-nitrophenyl)-5-phenyl-2H-tetrazolium chloride), and XTT (2,3-bis(2-methoxy-4-nitro-S-sulfophenyl)-5-[(phenylamino) carbonyl]-2H-tetrazolium hydroxide). The tetrazolium salt such as WST-4, WST-5, WST-8, NBT, INT, and XTT generates a formazan dye when reduced. The detection of this dye enables histamine to be detected. In one embodiment, the chromogenic reaction of the coloring reagent upon oxidation of histamine is promoted (facilitated) via the mediator. In one embodiment, the measurement reagent of the present invention comprises the coloring reagent having a final concentration of 0.1 mM or higher, 0.2 mM or higher, 0.3 mM or higher, 0.4 mM or higher, or 0.5 mM or higher, and 10 mM or lower, 5 mM or lower, or 2 mM or lower, for example, 0.1 mM to 10 mM, 0.5 mM to 2 mM or 1.1 mM, at the time of measurement or storage.

In one embodiment, the histamine measurement reagent of the present invention may further comprise a buffer. Examples of the buffer include a buffer that contains a compound having a zwitterion and having no carboxy group is selected from the group consisting of BES, MOPS, TES, HEPES, EPPS, TAPS, CHES, CAPS, TAPSO, POPSO, HEPPSO, ACES, Bis-Tris, MES, MOPSO, and PIPES, and Tris and a carbonate buffer. The buffer containing a compound having a zwitterion and having no carboxy group is preferably selected from the group consisting of BES, MOPS, TES, HEPES, EPPS, TAPS, CHES, CAPS, TAPSO, POPSO, and HEPPSO, and more preferably selected from the group consisting of HEPES, TAPSO, POPSO, HEPPSO, and EPPS. In one embodiment, the buffer may be a buffer that contains a compound having a zwitterion and having a sulfo group and is selected from the group consisting of BES, MOPS, TES, HEPES, EPPS, TAPS, CHES, CAPS, TAPSO, POPSO, HEPPSO, ACES, MES, MOPSO, and PIPES, preferably the group consisting of BES, MOPS, TES, HEPES, EPPS, TAPS, CHES, CAPS, TAPSO, POPSO, and HEPPSO, or may be Tris or a carbonate buffer. In one embodiment, the buffer may be a buffer that contains a compound having a zwitterion, having a sulfo group, and having a hydroxy group at position 2, and is selected from the group consisting of TAPSO, POPSO, HEPPSO, and MOPSO, preferably the group consisting of TAPSO, POPSO, and HEPPSO, or may be Tris or a carbonate buffer. The pH of the buffer is preferably on the order of 6.0 to 11.0 and can be more preferably 7.0 or higher, 8.0 or higher or 8.5 or higher, and 10.0 or lower or 9.5 or lower, for example, approximately 8.5 to 9.5. As for the concentration of the buffer, the final concentration at the time of measurement or storage, preferably at the time of measurement, can be, for example, 1 mM or higher, 10 mM or higher, or 150 mM or higher, and 300 mM or lower, 200 mM or lower, or 150 mM or lower, for example, 1 mM to 300 mM, 50 mM to 150 mM, or about 100 mM.

In one embodiment, the histamine measurement reagent of the present invention or the kit of the present invention may further comprise an extracting liquid for extracting histamine from a sample which may contain histamine. Extracting liquids known in the art can be used and for example, trichloroacetic acid, methanol, or a neutral phosphate buffer (JP Patent Publication (Kokai) No. 2001-099803 A (2001)), or an extracting liquid containing a chelating agent (JP Patent Publication (Kokai) No. 2004-129597 A (2004)) can be used, and water or various buffers can also be used. The measurement reagent of the present invention or the kit of the present invention may comprise an additional component (e.g., sugar (lactose, maltose, galactose, sucrose, glucose, trehalose, etc.), starch (including soluble starch), and dextrin (including branched dextrin, cyclodextrin, and highly branched cyclic dextrin (cluster dextrin))) and/or instructions for use.

In one embodiment, the kit of the present invention may comprise a sample collection part and a reaction part. The sample collection part is not particularly limited as long as the sample collection part is capable of collecting a sample which may contain histamine and examples thereof include cotton-tipped swabs, sponges, porous plastics, filter papers, nonwoven fabrics, and droppers. The sample collection part is preferably in the shape of, for example, a rod, and particularly preferably the shape of a rod having a fibrous or spongy wiping portion, for example, a cotton-tipped swab, from the perspective of convenient sample collection.

The reaction part is a site where reaction occurs when histamine is present in the sample collected by the sample collection part. In one embodiment, the reaction part comprises a histamine measurement reagent. In one embodiment, the histamine measurement reagent contained in the reaction part comprises histamine dehydrogenase and a reagent for colorimetry, or an anti-histamine antibody and a reagent for immunochromatography. In one embodiment, the histamine dehydrogenase and boric acid or a salt thereof, and/or the boronic acid or a salt thereof, and/or alkyl sulfate described in the present specification may be contained in a form contained in a solution such as the buffer described above or in a form contained as a freeze-dried product in the sample collection part or the reaction part in the kit of the present invention. The reaction part is preferably a transparent container through which the presence or absence of color development can be visually observed to detect histamine.

In one embodiment, the kit of the present invention may comprise an extraction part in addition to the sample collection part and the reaction part. The extraction part is a site where histamine is extracted into an extracting liquid when this histamine is present in the sample collected by the sample collection part. In one embodiment, the extraction part comprises a histamine measurement reagent. In one embodiment, the histamine measurement reagent contained in the extraction part comprises histamine dehydrogenase and a reagent for colorimetry, or an anti-histamine antibody and a reagent for immunochromatography. In one embodiment, the histamine dehydrogenase and boric acid or a salt thereof, and/or the boronic acid or a salt thereof, and/or alkyl sulfate described in the present specification may be contained in a form contained in a solution such as the buffer described above or in a form contained as a freeze-dried product in the extraction part in the kit of the present invention. The sample containing histamine extracted by the extraction part can be transferred to the reaction part where reaction is then performed.

In the present specification, "detection" of histamine includes detection of the presence or absence of histamine as well as quantification of histamine. Quantification of histamine can be performed based on the degree of color development in the case of using a chromogenic substrate. The quantification can be performed, preferably based on a calibration curve, for example, by using a plurality of, for example, 2 or more, preferably 3 or more, 4 or more, or 5 or more samples containing known concentrations of histamine, and comparing the sample in question with these (known) samples.

In one embodiment, the measurement reagent of the present invention or the kit of the present invention may comprise histamine dehydrogenase, an error reaction suppressor (e.g., boric acid or a salt thereof, and/or a boronic acid or a salt thereof), a mediator, and a coloring reagent. In another embodiment, the kit of the present invention may comprise histamine dehydrogenase, an error reaction suppressor (e.g., boric acid or a salt thereof, and/or a boronic acid or a salt thereof), and a mediator.

In one embodiment, the present invention provides a histamine measurement apparatus. This apparatus comprises a sample collection part, a reaction part, a sensor part and an instruction for use, or has an accompanying instruction for use and comprises a sample collection part, a reaction part, and a sensor part. The reaction part may comprise histamine dehydrogenase. The instruction for use states that sampling from a specimen is to be performed non-invasively. The sensor part has a sensor for the electrochemical measurement of histamine. This apparatus can be used for the examination of histamine food poisoning.

2. Method for Detecting Histamine

In one aspect, the present invention provides a method for detecting histamine using (i) histamine dehydrogenase and (ii) an error reaction suppressor for a sample collected by non-invasive sampling. Examples of the error reaction suppressor include (ii-a) boric acid or a salt thereof, and/or a boronic acid or a salt thereof, and/or (ii-b) alkyl sulfate. Any of other error reaction suppressors described in the present specification may also be used.

The method for detecting histamine according to the present invention may comprise the steps of: oxidizing histamine with histamine dehydrogenase (hereinafter, also referred to as an "oxidation step"); and detecting the oxidation of histamine with histamine dehydrogenase (hereinafter, also referred to as a "detection step").

The oxidation step can be performed by a method known to those skilled in the art. The oxidation step can be performed, for example, by mixing a sample which may contain histamine with a solution containing the histamine dehydrogenase described in the present specification.

The detection step can also be performed by a method known to those skilled in the art. The detection of the oxidation of histamine can be performed, for example, using a coloring reagent and optionally further using a mediator. The presence or absence of histamine can be detected, or the existing amount thereof can be measured, based on the presence or absence or the degree of oxidation in the oxidation step.

In addition to the oxidation step and the detection step, the method for detecting histamine according to the present invention may comprise a non-invasive sample collection step and/or a histamine extraction step before the oxidation step.

In the sample collection step, sampling is performed in a manner suitable for the method of the present invention, i.e., non-invasively, from a sample in which histamine is to be measured. Sampling (also referred to as sample collection) can be performed, for example, by non-invasively contacting a sample collection part such as a cotton-tipped swab, a sponge, a porous plastic, a filter paper, a nonwoven fabric, or a dropper, particularly preferably a sample collection part in the shape of a rod having a fibrous or spongy wiping portion, for example, a cotton-tipped swab, with a sample in which histamine is to be measured.

In the histamine extraction step, the subsequent oxidation step and detection step are facilitated by extracting histamine from the non-invasively collected sample. The histamine extraction step can be performed by mixing the sample for which histamine is to be measured (e.g., when the method of the present invention comprises a non-invasive sample collection step, the collection part into which the sample has been collected) with a histamine-extracting liquid. A histamine-extracting liquid known in the art can be used and for example, trichloroacetic acid, methanol, or a neutral phosphate buffer (JP Patent Publication (Kokai) No. 2001-099803 A (2001)), or an extracting liquid containing a chelating agent (JP Patent Publication (Kokai) No. 2004-129597 A (2004)), water or various buffers can also be used.

In an embodiment, by using the method or the kit of the present invention, histamine food poisoning may be prevented or avoided. That is, in one embodiment, when histamine is detected in an amount that may cause histamine food poisoning from a specimen as a result of measuring the specimen by using the method or the kit of the present invention, it can be concluded that this specimen need not be eaten, need not be subjected to food processing, or may be disposed of. In an embodiment, whether or not to accept (receive) an inspected fish during acceptance inspection of arrival of fish can be determined by rapidly and conveniently performing histamine measurement by using the method or the kit of the present invention. That is, in an embodiment, when histamine is detected in an amount that may cause histamine food poisoning from a fish specimen as a result of measuring the fish specimen by using the method or the kit of the present invention, it can be concluded that this fish specimen need not be accepted. Further, even if a minute amount of histamine is detected from a specimen at the stage of acceptance inspection, as long as subsequent quality control, temperature control, safety control in processing and cooking methods, etc. is carried out thoroughly, production of processed food or offering of fish meat for meals without the increase of histamine amount becomes possible.

For detecting cooking ingredients contaminated with histamine-producing microbes, it is important to confirm that histamine contents in edible parts do not exceed a given level. However, histamine contents are not fixed and are ever-changing due to production by the histamine-producing microbes. Even if the histamine content is small in an edible part at an initial stage, if the specimen contains a histamine-producing microbe and is preserved in poor conditions, the histamine content might differ between that at the time of acceptance inspection and that at the time of processing. On the other hand, in a specimen free from contamination by a histamine-producing microbe, it is believed that histamine content seldom increases over time. What is important for histamine examination in acceptance inspection of raw materials to sensitively and rapidly confirm whether or not the specimen has the risk of further increase in histamine content over time, i.e., whether or not the specimen is contaminated with a histamine-producing microbe, in addition to the degree of histamine contained in an edible part of the specimen. Thus, in an embodiment, the present invention provides a method for confirming whether or not a specimen is contaminated with a histamine-producing microbe. By using the method or the kit of the present invention, risk can be detected early at the stage when histamine content in an edible part is minute (very small) and the method of handling the cooking ingredient can be determined according to the results. In an embodiment, for example, when a minute amount of histamine is detected from a fish specimen as a result of measuring the fish specimen by using the method or the kit of the present invention, the fish can be subjected to quality control, temperature control, and processing and cooking under conditions where the histamine-producing microbe does not further proliferate in the fish specimen. In another embodiment, when a minute amount of histamine is detected from a fish specimen as a result of measuring the fish specimen by using the method or the kit of the present invention, guidance (instructions) can be given such that the fish should be subjected to quality control, temperature control, and processing and cooking under conditions such that the histamine-producing microbe does not further proliferate in the fish specimen. Thus, after acceptance inspection by the method or the kit of the present invention, the method of handling a cooking ingredient such as a fish can be determined according to the inspection results.

In an embodiment, histamine at an amount that may cause histamine food poisoning refers to histamine having a concentration higher than 50 ppm or a concentration of 60 ppm or higher, 70 ppm or higher, 80 ppm or higher, 90 ppm or higher, or 100 ppm or higher. In an embodiment, a minute amount of histamine that requires quality control or temperature control under conditions where the histamine-producing microbe does not further proliferate refers to histamine having a concentration of 20 ppm or lower. 30 ppm or lower, or 40 ppm or lower, for example, lower than 50 ppm. The reference value (standard value) of histamine acceptable for foods or edible parts thereof is not set in Japan. In other countries, the reference value is set to 100 ppm in Codex or EU and 50 ppm in the USA, for example, for main fishes and fishery processed products. Those skilled in the art can appropriately set a voluntarily imposed control reference value for handling a specimen with a histamine content as an index based on the reference value described in the present specification or set by each country.

In an embodiment, the present invention relates to a histamine measurement method for the examination of histamine food poisoning or for the prevention of histamine food poisoning, comprising the steps of:

(i) non-invasively sampling a specimen to obtain a sample for measurement from the specimen;

(ii) subjecting the sample obtained by the sampling in step (i) to histamine measurement; and (iii) determining whether or not the specimen causes histamine food poisoning, or whether or not the specimen is contaminated with a histamine-producing microbe, based on the results of the histamine measurement in step (ii).

According to the present invention, histamine contained in a specimen can be measured without destroying the specimen. In an embodiment, according to the present invention, histamine can be measured rapidly and conveniently. In an embodiment, according to the present invention, for example, the frequency of examination of fish, chicken meat, or the like can be increased. In another embodiment, according to the present invention, full inspection of all specimens is achieved (all specimens can be tested).

EXAMPLES

Examples given below are merely for illustration purposes and do not intend to limit the technical scope of the present invention in any way. Reagents are commercially available, or are obtained or prepared according to approaches commonly used in the art or procedures of literatures known in the art, unless otherwise specified.

Example 1: Preparation of a Calibration Curve 0.2 mL of a histamine measurement reagent containing 2% trehalose, 1.08 mM NBT, 41.5 μM 1-methoxy PMS and 0.128 U histamine dehydrogenase (prepared according to JP Patent Publication (Kokai) No. 2001-157597 A (2001)) was collected into each measurement tube and freeze-dried. One individual sardine fish was filleted (sliced into three) and finely minced into paste for homogenization using a kitchen knife, and a 1 g aliquot was collected into a polystyrene test tube. 1 mL of sterilized water was added to the test tube, mixed using a spatula, and then stirred for 10 seconds with a vortex mixer. This solution was sampled using cotton-tipped swabs (cotton tip part: approximately $4.5 mm) and then, histamine solutions having varying known concentrations were prepared for a calibration curve preparation, and 10 μL aliquots were then added to the cotton-tipped swabs.

Each cotton-tipped swab was pushed into a container loaded with 0.4 mL of 0.1 M HEPPSO buffer containing 0.1 M sodium tetraborate decahydrate and 0.1 M disodium citrate trihydrate with pH adjusted to 9.0 as an extracting liquid. The whole amount of the extracting liquid was shaken down to the measurement tube and reacted with the histamine measurement reagent.

Figure 1B:
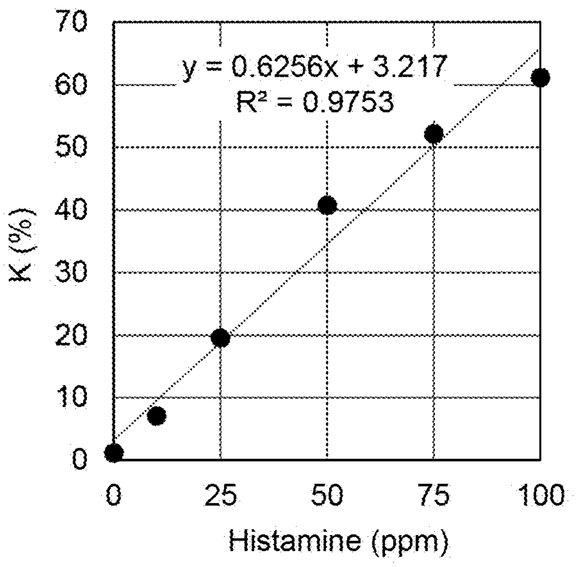

Results are shown in FIGS. 1A and 1B. As shown in FIGS. 1A and 1B it was found that histamine contained in a sample can be visually detected and its approximate concentration can also be measured.

For the purpose of confirming the visual determination as shown in FIGS. 1A and 1B by also using numerical data, colors were digitized by the following method: photographs of the measurement reagent tubes after color development were taken using STYLUS TG-4 Tough (manufactured by Olympus Corp.). Then, colors at or near the center of the images of the measurement tubes were converted to numerical values of CMYK (cyan, magenta, yellow, and black). That is, ILLUSTRATOR CS2™ (manufactured by Adobe Inc.) was used, and the center or its neighborhood of the measurement tube photographs was selected with the Eye-Dropper Tool in the Toolbox and the colors were digitized by confirming numerical values (%) through conversion into CMYK color codes in the Color Palette. For digitization, the "value of K" was used in all cases. A favorable correlation between K values and histamine concentrations was obtained in the presence of 0 to 100 ppm histamine, indicating that histamine can be quantified by digitization.

Example 2: Histamine Content Measurement of Sample 0.2 mL of a histamine measurement reagent containing 2% trehalose, 1.08 mM NBT, 41.5 μM 1-methoxy PMS and 0.128 U histamine dehydrogenase (prepared according to JP Patent Publication (Kokai) No. 2001-157597 A (2001)) was collected into each measurement tube and freeze-dried.

Sardine or horse mackerel was provided and cotton-tipped swabs (cotton tip part: approximately ϕ4.5 mm) were used to perform approximately 5 cm insertion from the edge of the mouth and approximately 2 cm insertion from the anus, and swabbing of the gills from gill slits and fish body surface. The mouth, the oral cavity, the esophagus, and a portion of the stomach of the fish specimens could be sampled by the 5 cm insertion of the cotton-tipped swab from the mouth. Also, the anus and a portion of the guts could be sampled by the 2 cm insertion of the cotton-tipped swab from the anus. The same holds true for other experiments.

Then, the inside of the peritoneal cavity immediately after gutting, the inside of the peritoneal cavity after washing, a fillet itself, and meat around the backbone were each swabbed. Further, an edible part was finely minced into paste for homogenization using a kitchen knife, and a 1 g aliquot was collected into a polystyrene test tube. 1 mL of sterilized water was added to the test tube, mixed using a spatula, and then stirred for 10 seconds with a vortex mixer. The resulting solution was sampled using cotton-tipped swabs. A container loaded with 0.4 mL of 0.1 M HEPPSO buffer containing 0.1 M sodium tetraborate decahydrate and 0.1 M disodium citrate trihydrate with pH adjusted to 9.0 as an extracting liquid was set in an upper part containing the histamine measurement reagent. The cotton-tipped swab having the sample of each location was pushed into the extracting liquid container and the whole amount of the extracting liquid was shaken down to the measurement tube and reacted with the histamine measurement reagent.

The mince was tested according to Histamine Test (Japanese product name Check Color Histamine, manufactured by Kikkoman Biochemifa Company) to measure the histamine content thereof. No histamine was detected in the samples of both fish (the number of trials per individual: in duplicate).

Figure 2A:
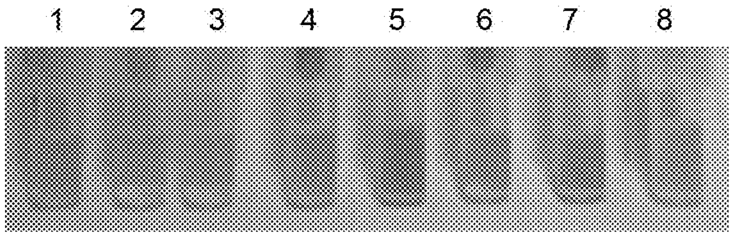
FIGS. 2A and 2B show results of sampling and measuring various sites of histamine ND (not detectable) samples (FIG. 2A: sardine, FIG. 2B: horse mackerel). 1 depicts the results of the mouth, 2 depicts the results of fish body surface, 3 depicts the results of the anus, 4 depicts the results of a gill slit, 5 depicts the results of the inside of the peritoneal cavity washed after gutting, 6 depicts the results of meat around the backbone after filleting, 7 depicts the results of a fillet, 8 depicts the results of mince, which were obtained by sampling and measurement by respective methods.
Figure 2B:
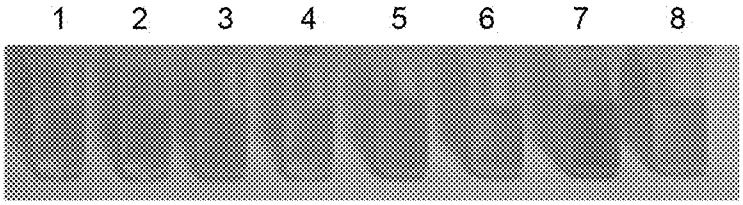

FIGS. 2A and 2B show the results of sampling various sites of the fishes using cotton-tipped swabs, and measuring histamine.

For the purpose of confirming the visual determination as shown in FIGS. 2A and 2B by also using numerical data, colors were digitized in the same manner as in Example 1. For digitization, the "value of K" was used in all cases. Numerical values obtained from the samples left for 15 minutes are shown in Table 1 below.

TABLE 1

| Site | Color(K Value) Sardine | Horse mackerel |
|---|---|---|
| Mouth | 1.96 | 0.78 |
| Body surface | 0.39 | 1.57 |
| Anus | 0 | 0.78 |
| Gill slit | 1.57 | 0 |
| Peritoneal cavity (washed) | 5.49 | 0.39 |
| Meat around backbone | 0.39 | 0 |
| Fillet | 1.96 | 3.53 |
| Mince 1 | 0 | 0 |

As shown in FIG. 2A, FIG. 2B and Table 1, no color development was seen at various sites of the fishes, confirming that it could accurately be measured that histamine was not detected (ND).

Example 3: Measurement of Histamine Detection Sample by Acceleration Test 0.2 mL of a histamine measurement reagent containing 2% trehalose, 1.08 mM NBT, 41.5 μM 1-methoxy PMS and 0.128 U histamine dehydrogenase (prepared according to JP Patent Publication (Kokai) No. 2001-157597 A (2001)) was collected into each measurement tube and freeze-dried.

Three individual fish of sardine or horse mackerel were provided as samples. Before the acceleration test, approximately 5 cm insertion from the edge of the mouth and approximately 2 cm insertion from the anus, and swabbing of fish body surface and the gills (horse mackerel only) were performed as non-invasive sampling using cotton-tipped swabs. After sampling, all samples were left at 20° C. for 18 hours. Non-invasively samplable sites of the samples left as above were first sampled using cotton-tipped swabs in the same manner as above. More specifically, approximately 5 cm insertion from the edge of the mouth and approximately 2 cm insertion from the anus, swabbing of the gills and fish body surface, and collection of a drip (horse mackerel only) were performed. The drip was collected only from feasible samples.

Then, the inside of the peritoneal cavity immediately after gutting, the inside of the peritoneal cavity after washing, a fillet itself, and meat around the backbone were each swabbed. Further, an edible part was finely minced into paste for homogenization using a kitchen knife, and a 1 g aliquot was collected into a polystyrene test tube. I mL of sterilized water was added to the test tube, mixed using a spatula, and then stirred for 10 seconds with a vortex mixer. The resulting solution was sampled using cotton-tipped swabs.

A container loaded with 0.4 mL of 0.1 M HEPPSO buffer containing 0.1 M sodium tetraborate decahydrate and 0.1 M disodium citrate trihydrate with pH adjusted to 9.0 as an extracting liquid was set in an upper part containing the histamine measurement reagent. The cotton-tipped swab having the sample of each location was pushed into the extracting liquid container and the whole amount of the extracting liquid was shaken down to the measurement tube and reacted with the histamine measurement reagent. Histamine content in the mince was quantified using Histamine Test.

Figure 3A:
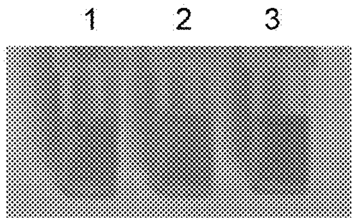
FIGS. 3A and 3B show results of non-invasively sampling sardine (FIG. 3A) or horse mackerel (FIG. 3B) before an acceleration test, and measuring histamine contents. 1 depicts the sampling results of the mouth, 2 depicts the sampling results of fish body surface, 3 depicts the sampling results of the anus, 4 depicts the sampling results of a gill slit (horse mackerel only). Horse mackerel (1) to (3) are different individual specimens.
Figure 3B:
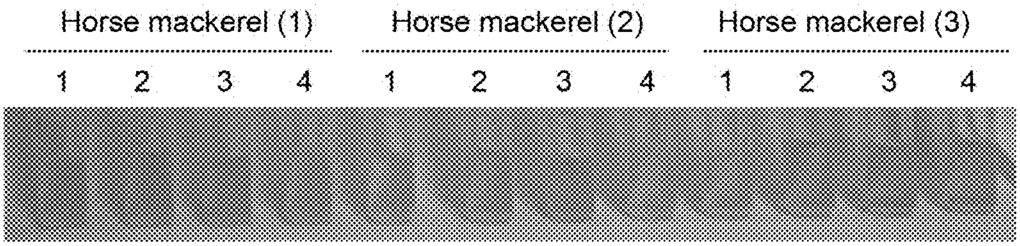

The results obtained before preservation at 20° C. are shown in FIGS. 3A and 3B (FIG. 3A: sardine, FIG. 3B: horse mackerel). For the purpose of confirming the visual determination as shown in FIGS. 3A and 3B by also using numerical data, colors were digitized in the same manner as in Example 1. For digitization, the "value of K" was used in all cases. Numerical values obtained from the samples left for 15 minutes are shown in Table 2 below.

TABLE 2

| Site | Color Sardine (1) | Horse mackerel (1) | Horse mackerel (2) | Horse mackerel (3) |
|---|---|---|---|---|
| Mouth | 1.96 | 3.53 | 0 | 0 |
| Body surface | 2.35 | 3.53 | 0.39 | 0 |
| Anus | 5.1 | 1.18 | 0 | 0 |
| Gill slit | | 0.39 | 0 | 0.78 |

As shown in FIG. 3A, FIG. 3B and Table 2, no color development was seen in the samples before the acceleration test. The numerical values compared with the calibration curve of Example 1 were 10 ppm or lower for all of the sites and were also consistent with the results of Example 2.

The histamine contents measured with Histamine Test in the samples preserved at 20° C. are shown in Table 3. The results of measurement with cotton-tipped swabs are shown in FIGS. 4A and 4B.

TABLE 3

| Histamine concentration(ppm) Sardine (1) | Sardine (2) | Sardine (3) | Horse mackerel (1) | Horse mackerel (2) | Horse mackerel (3) |
|---|---|---|---|---|---|
| 16 | 35 | 69 | 5 | 8 | 16 |

Figure 4A:
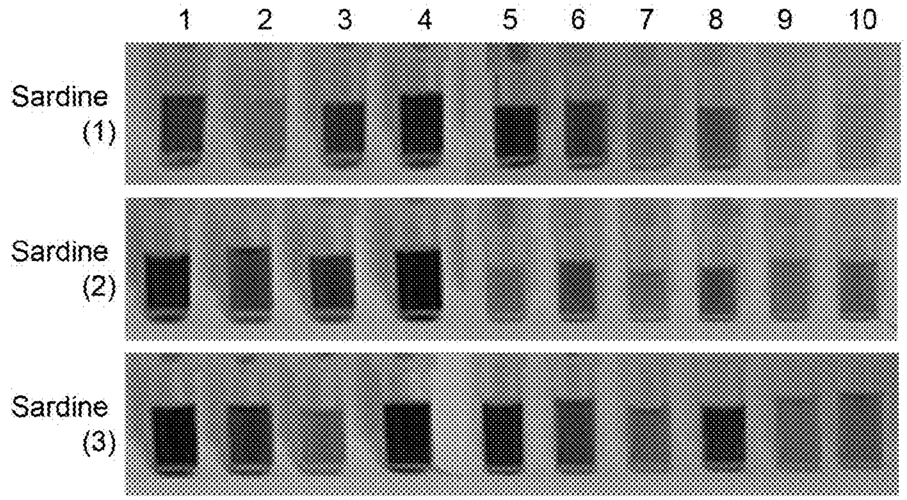
FIGS. 4A and 4B show results of measuring a histamine content in each of three individual specimens of sardine (FIG. 4A) or horse mackerel (FIG. 4B) after preservation at 20° C. for 18 hours. 1 depicts the results of the mouth, 2 depicts the results of fish body surface, 3 depicts the results of the anus, 4 depicts the results of a gill slit, 5 depicts the results of a drip (horse mackerel only), 6 depicts the results of the inside of the peritoneal cavity after gutting, 7 depicts the results of the inside of the peritoneal cavity after washing, 8 depicts the results of meat around the backbone after filleting, 9 depicts the results of a fillet, and both 10 and 11 depict the results of mince, which were obtained by sampling and measurement by respective methods. Sardine (1) to (3) are different individual specimens. Horse mackerel (1) to (3) are different individual specimens.
Figure 4B:
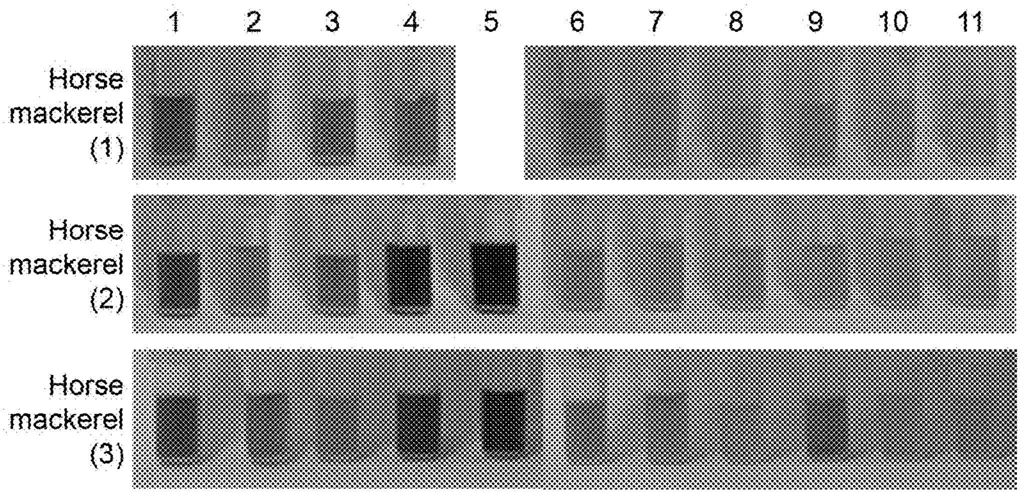

For the purpose of confirming the visual determination as shown in FIGS. 4A and 4B by also using numerical data, colors were digitized in the same manner as in Example 1. For digitization, the "value of K" was used in all cases. Numerical values obtained from the samples left for 15 minutes are shown in Table 4 below.

TABLE 4

| | Color | | | | | |
|---|---|---|---|---|---|---|
| Site | Sardine (1) | Sardine (2) | Sardine (3) | Horse mackerel (1) | Horse mackerel (2) | Horse mackerel (3) |
| Mouth | 47.06 | 63.14 | 68.63 | 38.82 | 40.78 | 38.82 |
| Body surface | 9.8 | 36.47 | 47.84 | 11.37 | 10.59 | 20 |
| Anus | 51.76 | 48.63 | 18.82 | 25.49 | 21.57 | 14.12 |
| Gill slit | 62.75 | 71.76 | 70.98 | 24.71 | 62.35 | 50.59 |
| Drip | | | | | 70.2 | 56.86 |
| Peritoneal cavity (unwashed) | 65.1 | 14.51 | 61.57 | 26.27 | 10.2 | 14.12 |
| Peritoneal cavity (washed) | 49.02 | 36.47 | 39.22 | 10.59 | 5.88 | 11.37 |
| Meat around backbone | 11.76 | 9.02 | 18.43 | 6.27 | 5.88 | 5.49 |
| Fillet | 27.45 | 30.98 | 53.73 | 7.84 | 4.31 | 27.84 |
| Mince 1 | 1.96 | 10.2 | 13.33 | 4.71 | 4.71 | 9.41 |
| Mince 2 | 1.57 | 17.65 | 22.35 | 4.31 | 4.31 | 12.94 |

As shown in Table 4, histamine was detected from all the samples preserved at 20° C. for 18 hours. As shown in FIGS. 4A and 4B, color development was also confirmed in almost all of the sites sampled with cotton-tipped swabs.

Table 5 shows a histamine concentration (value determined by taking the 2-fold dilution at the time of extraction into consideration) in each mince calculated from the calibration curve of Example 1 and the numerical values of Table 4.

TABLE 5

| Histamine concentration(ppm) | | | | | |
|---|---|---|---|---|---|
| Sardine (1) | Sardine (2) | Sardine (3) | Horse mackerel (1) | Horse mackerel (2) | Horse mackerel (3) |
| 10 or lower | 34 | 46 | 10 or lower | 10 or lower | 25 |

As shown in Tables 3 and 5, approximate correlation was obtained between the quantification values from Histamine Test and the color development from cotton-tipped swabs.

No color development was seen in the samples (obtained by non-invasive sampling) before the acceleration test believed to have ND (not detectable) levels of histamine. By contrast, in the samples (obtained by non-invasive sampling) preserved at 20° C., deep color development was confirmed in the mouth, the gill slits, the anus, and the drip even when histamine was detected with a low concentration (approximately dozen ppm). It is believed that this is because, since histamine-producing microbes propagate in the viscera, mainly in the guts, and gradually migrate to edible parts, histamine can be detected with high sensitivity at sites proximal to the viscera, as compared with examination in the edible parts. The method of the present invention was shown to be able to detect a minute amount of histamine present in an edible part by non-invasive sampling. It is believed that this permits full inspection of all samples and measurement of time-dependent change in histamine content, leading to prevention of large-scale food poisoning.

Example 4

While various histamine measurements were performed, a certain amount of color development was observed even in the case of using a system free from histamine and histamine dehydrogenase in some experiments (described below). This was believed to be due to error reaction. The degree of error color development corresponded to approximately 10 ppm by visual determination using colorimetry. It is believed that this margin of error can be accepted in histamine measurement for the examination of histamine food poisoning. However, for more accurate histamine measurement by colorimetry, substances inhibiting error color development were studied as described below.

<Experiment 1: Study on Coloring Reagent>

0.2 mL of a histamine measurement reagent containing 2% trehalose, a coloring reagent (1.08 mM WST-4, WST-5, WST-8, INT, NBT, or XTT), 41.5 μM 1-methoxy PMS, and 0.128 U histamine dehydrogenase (prepared according to JP Patent Publication (Kokai) No. 2001-157597 A (2001)) was collected into each measurement tube and freeze-dried. Histamine solutions having varying known concentrations were prepared for calibration curve preparation, and 0.1 mL aliquots were then added to cotton-tipped swabs. As for samples. 0.1 mL of a drip of tuna strip (Saku block tuna) was added to each cotton-tipped swab, or the surface of tuna strip was swabbed.

Each cotton-tipped swab was pushed into a container loaded with 0.4 mL of EDTA (2Na) with pH adjusted to 9.0 as an extracting liquid, which was further shaken down to the measurement tube where the extracting liquid was then reacted with the histamine measurement reagent.

As a result, it was found that histamine contained in a sample can be visually detected and its approximate concentration can also be measured by using any of the coloring reagents WST-4, WST-5, WST-8, NBT, INT, and XTT. Accordingly, for the purpose of confirming this visual determination by also using numerical data, colors were digitized in the same manner as in Example 1. Results are shown in the table below.

TABLE 6

| | | WST-4 | WST-5 | WST-8 | NBT | INT | XTT |
|---|---|---|---|---|---|---|---|
| | | | | Drip | | | |
| | | 33.3 | 42.8 | 20.0 | 20.0 | 25.5 | 26.7 |
| | | | | Swab | | | |
| | | 30.6 | 38.0 | 14.5 | 19.6 | 19.2 | 20.8 |
| Histamine concentration (ppm) | 0 | 9.0 | 12.6 | 4.7 | 4.7 | 6.7 | 6.7 |
| | 5 | 15.3 | 16.5 | 8.6 | 7.5 | 12.2 | 10.2 |
| | 10 | 24.7 | 23.9 | 10.6 | 12.6 | 19.6 | 15.7 |

TABLE 6-continued

| | WST-4 | WST-5 | WST-8 | NBT | INT | XTT |
|---|---|---|---|---|---|---|
| | | | Drip | | | |
| | 33.3 | 42.8 | 20.0 | 20.0 | 25.5 | 26.7 |
| | | | Swab | | | |
| | 30.6 | 38.0 | 14.5 | 19.6 | 19.2 | 20.8 |
| 25 | 40.0 | 46.7 | 16.5 | 27.1 | 38.4 | 25.1 |
| 50 | 56.5 | 64.3 | 21.6 | 40.4 | 54.9 | 29.4 |
| 100 | 67.1 | 71.4 | 28.6 | 51.8 | 68.6 | 34.5 |
| 150 | 71.8 | 72.9 | 32.2 | 57.7 | 72.2 | 36.9 |
| 200 | 71.8 | 72.9 | 33.7 | 63.9 | 74.1 | 37.7 |
| 300 | 72.9 | 72.6 | 38.0 | 66.7 | 74.9 | 39.2 |

Also, a test was conducted in a system free from histamine and histamine dehydrogenase as described below. That is, EDTA (2Na) was adjusted to 0.1 M and pH 8.5, and 0.4 mL of the resultant was added to a freeze-dried product of 0.2 mL of a reagent containing 2% trehalose, 1.08 mM NBT, and 41.5 μM 1-methoxy PMS. After mixing, the mixture was left at room temperature for 60 minutes, and the degree of color development was confirmed. As a result, a certain amount of color development (error reaction) was confirmed even in a system free from histamine and histamine dehydrogenase. For the purpose of confirming this visual determination by also using numerical data, colors were digitized in the same manner as above. For digitization, the "value of K" was used in all cases. The difference in color between before and after leaving the samples for 60 minutes was 27.45.

<Experiment 2: Study on Buffer-1>

In experiment 1, color development was observed even in histamine-free samples. Therefore, buffers were studied in order to inhibit (suppress) or reduce this error reaction.

EDTA (2Na), BES, MOPS, TES, HEPES, TAPSO, POPSO, HEPPSO, EPPS, Tricine, Bicine, TAPS, CHES, and CAPS were all adjusted to 0.1 M and pH 8.5, and 0.4 mL of the resultant was added to a freeze-dried aliquot of 0.2 mL of a reagent containing 2% trehalose, 1.08 mM NBT, and 41.5 μM 1-methoxy PMS. After mixing, the mixture was left at room temperature for 60 minutes, and the degree of color development was confirmed. As a result, error color development was suppressed by using the buffer. For the purpose of confirming this visual determination by also using numerical data, colors were digitized in the same manner as in Example 1. For digitization, the "value of K" was used in all cases. The difference in color between before and after leaving the samples for 60 minutes is shown in the table below.

TABLE 7

| Experimental system No. | Buffer | Color change |
|---|---|---|
| 1 | EDTA | 27.45 |
| 2 | BES | 1.96 |
| 3 | MOPS | 3.52 |
| 4 | TES | 0.4 |
| 5 | HEPES | 0 |
| 6 | TAPSO | 0 |
| 7 | POPSO | 0.39 |
| 8 | HEPPSO | 0 |
| 9 | EPPS | 0 |
| 10 | Tricine | 10.2 |

TABLE 7-continued

| Experimental system No. | Buffer | Color change |
|---|---|---|
| 11 | Bicine | 17.64 |
| 12 | TAPS | 5.88 |
| 13 | CHES | 8.63 |
| 14 | CAPS | 17.26 |

As shown in the table above, error color development seen in histamine-free samples was markedly suppressed (inhibited) in the experimental systems using HEPES, TAPSO, POPSO, HEPPSO, and EPPS buffers. BES, MOPS, TES, TAPS and CHES were also confirmed to have a tendency to suppress error reaction.

<Experiment 3: Study on Buffer-2>

EDTA (2Na), sodium bicarbonate/disodium carbonate, boric acid, and tris(hydroxymethyl)aminomethane were all adjusted to 0.1 M and pH 9.0, and 0.4 mL of the resultant was added to a freeze-dried product of 0.2 mL of a reagent containing 2% trehalose, 1.08 mM NBT, and 41.5 μM 1-methoxy PMS. After mixing, the mixture was left at room temperature for 60 minutes, and the degree of color development was confirmed.

As a result, suppression of error color development was observed. For the purpose of confirming this visual determination by also using numerical data, colors were digitized in the same manner as in Example 1. For digitization, the "value of K" was used in all cases. The difference in color between before and after leaving the samples for 60 minutes is shown in the table below.

TABLE 8

| Experimental system No. | Buffer | Color change |
|---|---|---|
| 1 | EDTA | 5.49 |
| 2 | Carbonic acid | 0.4 |
| 3 | Boric acid | 0 |
| 4 | Tris | 0.78 |

As shown in the table above, carbonic acid and boric acid exhibited an error reaction suppression effect.

<Experiment 4: Suppression of Error Reaction in Presence of Sample-1>

1 g of a fish meat sample (mackerel) finely minced using a kitchen knife was mixed with 1 ml of any of 1) a 0.1 M HEPPSO solution (pH 8.5), 2) a 0.1 M HEPPSO solution (pH 9.0), 3) a 0.1 M HEPPSO solution (pH 8.5) containing 25 mM boric acid, and 4) a 0.1 M HEPPSO solution (pH 9.0) containing 25 mM boric acid, thoroughly mixed using a spatula, and then stirred for 10 seconds with a vortex mixer for extraction. Each extracting liquid was collected using a cotton-tipped swab and the cotton-tipped swab was suspended in a polystyrene test tube containing 0.4 mL of any of the solutions 1) to 4) in advance, and the whole amount of the suspension was added to a freeze-dried product of 0.2 mL of a reagent containing 2% trehalose, 1.08 mM NBT, and 41.5 μM 1-methoxy PMS. After reaction, the mixture was left at room temperature for 60 minutes, and the degree of color development was confirmed. As a blank control, the reagent was dissolved in 0.4 mL of a 0.1 M HEPPSO solution (pH 8.5 or pH 9.0). Incidentally, the fish meat sample used above was a sample from which histamine was not detected by measuring the histamine content beforehand using Histamine Test (manufactured by Kikkoman Biochemifa Company). In this experiment system, no histamine dehydrogenase was included in the reaction system. In other words, not only was histamine non-existent in the fish meat sample, but further, even if a minute amount of histamine was present in the reaction system, histamine dehydrogenase was not included in the reaction system and, therefore, it is believed that histamine does not bring about color development.

However, as a result of the experiment above, coloring was observed even in the absence of histamine and histamine dehydrogenase. As seen from this, even if HEPPSO suppressed reagent-derived error reaction, when a sample such as fish meat was further added into the reaction system, HEPPSO could not completely suppress color development believed to be an error reaction not derived from histamine. On the other hand, by further adding boric acid to HEPPSO, even when a sample such as fish meat was added, color development believed to be an error reaction not derived from histamine could be significantly suppressed.

Further, for the purpose of confirming this visual determination by also using numerical data, colors were digitized in the same manner as in Example 1. For digitization, the "value of K" was used in all cases. The difference in color between before and after leaving the samples for 60 minutes is shown in the table below.

TABLE 9

| | | Color change |
|---|---|---|
| 25 mM boric acid | Sample | 0.39 |
| 0.1M HEPPSO pH 8.5 | Control | 0.39 |
| 25 mM boric acid | Sample | 2.75 |
| 0.1M HEPPSO pH 9 | Control | 0.39 |
| No boric acid | Sample | 4.7 |
| 0.1M HEPPSO pH 8.5 | Control | 1.18 |
| No boric acid | Sample | 39.22 |
| 0.1M HEPPSO pH 9 | Control | 4.71 |

As described above, error color development was seen at both pH 8.5 and 9.0 and even color development as large as color development equivalent to approximately 25 ppm using histamine standards, was observed, suggesting that error color development may cause misjudgment in histamine detection. It was also indicated that error color development can be suppressed by adding boric acid.

<Experiment 5: Suppression of Error Reaction in Presence of Sample-2>

1 g of a minced fish meat sample (mackerel) was subjected to extraction with 1 mL of 0.1 M HEPPSO (pH 8.5) containing 1) a control or 25 mM or lower boronic acid, 2) phenylboronic acid, 3) 4-chlorophenylboronic acid, 4) 4-fluorophenylboronic acid, 5) butylboronic acid, or 6) 3-[(tert-butoxycarbonyl)amino]phenylboronic acid. For extraction, the fish meat was thoroughly mixed with each extracting liquid using a spatula, and then stirred for 10 seconds with a vortex mixer. The extracting liquid was collected using a cotton-tipped swab. The cotton-tipped swab was suspended in a polystyrene test tube containing 0.4 mL of any of the solutions 1) to 6) in advance, and the whole amount of the suspension was added to a freeze-dried aliquot of 0.2 mL of a reagent containing 2% trehalose, 1.08 mM NBT, and 41.5 μM 1-methoxy PMS. After reaction, the mixture was left at room temperature for 60 minutes, and the degree of color development was confirmed.

As a result, suppression of error color development was observed. For the purpose of confirming this visual determination by also using numerical data, colors were digitized in the same manner as in Example 1. For digitization, the "value of K" was used in all cases. The difference in color between before and after leaving the samples for 60 minutes is shown in the table below.

TABLE 10

| Experimental system No. | Adduct | Color change |
|---|---|---|
| 1 | Control | 15.69 |
| 2 | Phenylboronic acid | 8.23 |
| 3 | 4-Chlorophenylboronic acid | 8.63 |
| 4 | 4-Fluorophenylboronic acid | 7.46 |
| 5 | Butylboronic acid | 7.45 |
| 6 | 3-[(tert-Butoxy-carbonyl)amino]phenylboronic acid | 1.57 |

As shown in the table above, by adding a boronic acid, sample-derived error reaction could be strongly suppressed and this effect was significant, particularly, when 3-[(tert-butoxycarbonyl)amino]phenylboronic acid was added.

<Experiment 6: Study on Boric Acid Concentration>

2 g of a minced fish meat sample (mackerel) was subjected to extraction in the same manner as in experiment 5 using 2 mL of 0.1 M HEPPSO (pH 8.5) containing boric acid at a concentration of each of 0) mM to 100 mM. A cotton-tipped swab was suspended in 0.4 mL of the extracting liquid, and the whole amount of the suspension was added to a freeze-dried product of 0.2 mL of a reagent containing 2% trehalose, 1.08 mM NBT, and 41.5 μM 1-methoxy PMS. After reaction, the mixture was left at room temperature for 60 minutes, and the degree of color development was confirmed. As a result, boric acid reduced error reaction in a concentration-dependent manner.

For the purpose of confirming this visual determination by also using numerical data, colors were digitized in the same manner as in Example 1. For digitization, the "value of K" was used in all cases. The difference in color between before and after leaving the samples for 60 minutes is shown in the table below.

TABLE 11

| Boric acid concentration (mM) | Color change |
|---|---|
| 0 | 7.84 |
| 1 | 5.88 |
| 2.5 | 5.49 |
| 10 | 5.1 |
| 25 | 3.92 |
| 50 | 0.78 |
| 75 | 0.78 |
| 100 | 0.79 |

As described above, boric acid reduced error reaction in a concentration-dependent manner.

<Experiment 7: Suppression of Error Reaction by SDS>

2 g of a minced fish meat sample (mackerel) was subjected to extraction in the same manner as in experiment 5 using 2 mL of 0.1 M HEPPSO (pH 8.0) containing SDS at a concentration of each of 0% to 1%. A cotton-tipped swab was suspended in 0.4 mL of the extracting liquid, and the whole amount of the suspension was added to a freeze-dried product of 0.2 mL of a reagent containing 2% trehalose, 1.08 mM NBT, and 41.5 μM 1-methoxy PMS. After reaction, the mixture was left at room temperature for 60 minutes, and the degree of color development was confirmed. As a result, SDS was also confirmed to reduce error reaction.

For the purpose of confirming this visual determination by also using numerical data, colors were digitized in the same manner as in Example 1. For digitization, the "value of K" was used in all cases. The difference in color between before and after leaving the samples for 60 minutes is shown in the table below.

TABLE 12

| SDS concentration | Color change |
|---|---|
| 0 | 23.53 |
| 0.1 | 1.17 |
| 1 | 1.57 |

As described above, SDS was also shown to reduce error reaction.

<Experiment 8: Confirmation that Boric Acid does not Inhibit Color Reaction>

2 g of a minced fish meat sample (mackerel) was subjected to extraction in the same manner as in experiment 5 using 2 mL of 0.1 M HEPPSO (pH 9.0) containing 25 mM or 100 mM boric acid. After the extraction, 0, 10, 25, 50, 75, or 100 ppm histamine was added to 0.4 mL of the extracting liquid. A cotton-tipped swab was suspended in this extracting liquid, and the whole amount of the suspension was added to a freeze-dried aliquot of 0.2 mL of a reagent containing 2% trehalose, 1.08 mM NBT, and 41.5 μM 1-methoxy PMS. After reaction, the mixture was left at room temperature for 15 minutes, and the degree of color development was confirmed. As a result, the addition of boric acid was confirmed to have no adverse effect on color development derived from histamine. For the purpose of confirming this visual determination by also using numerical data, colors were digitized in the same manner as in Example 1. For digitization, the "value of K" was used in all cases. The difference in color between before and after leaving the samples for 15 minutes is shown in the table below.

TABLE 13

| Histamine | Color change | |
|---|---|---|
| concentration (ppm) | 25 mM boric acid | 100 mM boric acid |
| 0 | 5.88 | 2.75 |
| 10 | 9.41 | 8.24 |
| 25 | 19.61 | 18.04 |
| 50 | 35.69 | 39.61 |
| 75 | 45.49 | 52.94 |
| 100 | 57.25 | 63.53 |

As shown in the table above, measurement was achieved even at a boric acid concentration of 100 mM, showing that the addition of boric acid has no adverse effect on color development derived from histamine.

As shown in the experiments described above, boric acid, a boronic acid compound of formula (1) or (II), alkyl sulfate, various buffers, etc. were able to suppress error reaction (error color development). The histamine measurement method of the present invention does not necessarily require such a compound. However, by using such error reaction suppressor even more accurate measurement of histamine becomes possible. Therefore, such an error reaction suppressor can be used in the histamine measurement of the present invention.

INDUSTRIAL APPLICABILITY

According to the present invention, when measuring histamine, the specimen need not be destroyed (minced) and non-invasive histamine examination can be achieved. This also enables histamine to be detected non-destructively even for, for example, fish meat that is provided per se in meals.

The present invention is described above with reference to the examples. However, various changes or modifications can be made therein without departing from the spirit of the present invention.

All publications, patents and patent applications cited herein are incorporated herein by reference in their entirety.

The invention claimed is:

1. A method of measuring only histamine for the examination of histamine food poisoning or for the prevention of histamine food poisoning, comprising the steps of:
(i) non-invasively sampling a specimen to obtain a sample for measurement from the specimen; and
(ii) subjecting the sample obtained by the sampling in step (i) to a histamine measurement,
wherein the histamine measurement is measured by colorimetry using an enzyme, wherein the enzyme consists of a histamine dehydrogenase, and a mediator, or by immunochromatography using an anti-histamine antibody,
wherein the sample for measurement is collected without damaging the specimen for the sampling,
wherein the specimen is a fish or a chicken, and wherein
when the specimen is a fish, the non-invasive sampling is performed from the mouth, a gill slit, anus, or peritoneal cavity, or
when the specimen is a chicken, the non-invasive sampling is performed from the mouth, anus, or on a surface of a cut of chicken meat that is not minced.

2. The method according to claim 1, wherein the non-invasive sampling is performed by swabbing using a cotton tipped swab.

3. The method of claim 1, wherein the histamine dehydrogenase acts on histamine without acting on cadaverine or putrescine.

4. A method of measuring histamine for the examination of histamine food poisoning or for the prevention of histamine food poisoning, the method comprising the steps of:
(i) non-invasively sampling a specimen to obtain a sample for measurement from the specimen; and
(ii) subjecting the sample obtained by the sampling in step (i) to a histamine measurement,
wherein the histamine measurement is measured by colorimetry using a histamine dehydrogenase and a mediator or by immunochromatography using an anti-histamine antibody, and further using an error reaction suppressor,
wherein the sample for measurement is collected without damaging the specimen for the sampling,
wherein the specimen is a fish or a chicken, and wherein
when the specimen is a fish, the non-invasive sampling is performed from the mouth, a gill slit, anus, peritoneal cavity, on a surface of the fish body, or on a surface of a cut of fish meat that is not minced, or
when the specimen is a chicken, the non-invasive sampling is performed from the mouth, anus, or on a surface of a cut of chicken meat that is not minced,
wherein the error reaction suppressor is at least one selected from the group consisting of:

(1) boric acid or a salt thereof;

(2) a boronic acid represented by the following formula (I) or (II):

(I)

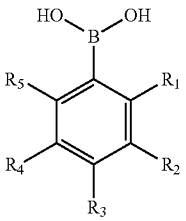

or (II)

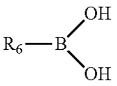

wherein $R_1$, $R_2$, $R_3$, $R_4$ and $R_5$ are each independently selected from the group consisting of H, a boronyl group, a halogen group, a hydroxy group, a carboxy group, a nitro group, an amino group, a sulfo group, a thiol group, a tert-butoxycarbonylamino group, a substituted or unsubstituted $C_1$ to $C_{10}$ alkyl group, a substituted or unsubstituted alkenyl group, and a substituted or unsubstituted alkynyl group, and $R_6$ is selected from the group consisting of a substituted or unsubstituted $C_1$ to $C_{10}$ alkyl group, a substituted or unsubstituted alkenyl group, and a substituted or unsubstituted alkynyl group, wherein the substituted $C_1$ to $C_{10}$ alkyl group, the substituted alkenyl group or the substituted alkenyl group is substituted with at least one substituent selected from the group consisting of a boronyl group, a halogen group, a hydroxy group, a carboxy group, a nitro group, an amino group, a sulfo group and a thiol group, or a salt thereof;

(3) alkyl sulfate; and (4) a buffer selected from the group consisting of BES, MOPS, TES, HEPES, EPPS, TAPS, CHES, CAPS, TAPSO, POPSO, HEPPSO, ACES, Bis-Tris, MES, MOPSO, PIPES, Tris (tris(hydroxymethyl)aminomethane), and a carbonate buffer.

* * * * *